United States Patent [19]

Belykh et al.

[11] 4,375,810

[45] Mar. 8, 1983

[54] JOINING ELEMENT FOR FIXATION OF BONE TISSUES

[76] Inventors: Sergei I. Belykh, 2 Krestovsky pereulok, 4, kv. 66; Anatoly B. Davydov, ulitsa Krasny Kazanets, 19, korpus 1, kv. 28; Igor L. Kovalenko, ulitsa Chapaeva, 7, kv. 30; Lidia Y. Loktionova, ulitsa Skryabina, 25/1, korpus 2, kv. 49, all of, Moscow; Anatoly D. Moschensky, Malakhovka, Bykovskoe shosse, 41, kv. 66, Moskovskaya oblast; Gely G. Pershin, Krivorozhskaya ulitsa, 9, kv. 62, Moscow; Grigory N. Pershin, ulitsa Ulbrikhta, 19/10, kv. 75, Moscow; Elena N. Padeiskaya, Leninsky prospekt, 13, kv. 24, Moscow; Lidia M. Polukhina, Alleya Zhemchugovoi, 3, korpus 1, kv.2, Moscow; Nikolai I. Ochirov, Tashkentskaya ulitsa, 34, korpus 2, kv. 195, Moscow; Jury I. Filippov, Zaraiskaya ulitsa, 41, kv. 55, Moscow, all of U.S.S.R.

[21] Appl. No.: 109,529

[22] Filed: Jan. 4, 1980

[30] Foreign Application Priority Data

Jan. 4, 1979 [SU] U.S.S.R. .................... 2712921

[51] Int. Cl.³ .................... A61F 5/04; A61F 1/00
[52] U.S. Cl. .................... 128/92 R; 3/1.9
[58] Field of Search .................... 128/92, 92 B, 92 BA, 128/92 BB, 92 BC, 92 C, 92 D; 3/1.9, 1.913

[56] References Cited

U.S. PATENT DOCUMENTS

| 3,767,437 | 10/1973 | Cruz, Jr. .................... 3/1.9 X |
| 3,893,196 | 7/1975 | Houtman .................... 3/1.913 X |
| 4,164,794 | 8/1979 | Spector et al. .................... 3/1.9 |

FOREIGN PATENT DOCUMENTS 2400134 1/1974 Fed. Rep. of Germany .......... 3/1.9

Primary Examiner—Stephen C. Pellegrino
Attorney, Agent, or Firm—Burgess, Ryan & Wayne

[57] ABSTRACT

According to the present invention there is provided a joining element for fixing bone tissues, which is made essentially as an oblong solid provided with recesses, wherein are made fast inserts of a biologically compatible polymer, containing a physiologically active medical preparations.

2 Claims, 6 Drawing Figures

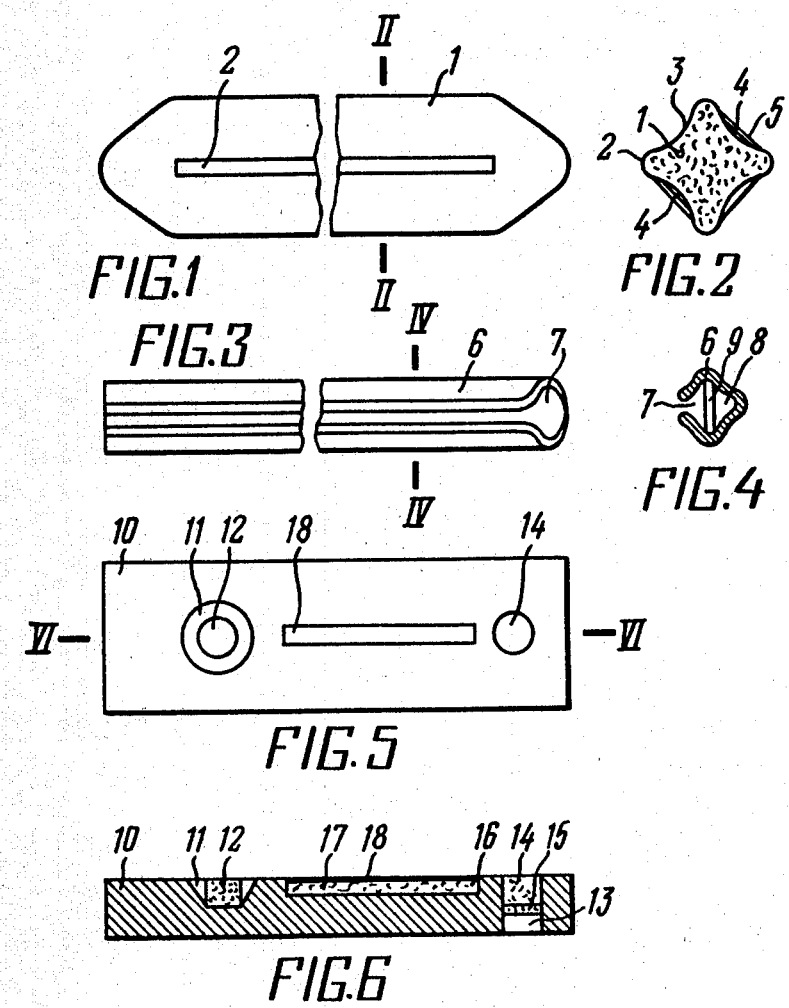

JOINING ELEMENT FOR FIXATION OF BONE TISSUES

1. TECHNICAL FIELD

The present invention relates generally to medicine and more specifically to joining elements for fixing bone tissues.

2. BACKGROUND ART

The present-day state of traumatology and orthopedics knows a method of uniting bone fragments through the use of diverse joining elements, such as rods for intramedullary fixation (cf. a textbook "Intramedullary fixation with a metallic rod in fractures of long tubular bones" by Ya. T. Dubov, Medgiz Publishers, 1961 Moscow), rods of polymer materials (cf. USSR Inventor's Certificate No. 601,948), or cover plates (cf. a textbook "Essentials of traumatology and orthopedics" by A. P. Skoblin, Meditsina Publishers, Moscow 1974, p. 136).

All of the aforesaid joining elements are disadvantageous in that they can perform only a passive role as fixing members of bone fragments, and in some cases happen to be causative of an onset of some undesirable processes (such as purulent inflammations, irritations, resorption of bone tissue, etc.).

3. OBJECT OF THE INVENTION

An object of the present invention is to provide such a joining element that would be instrumental in producing a physiological effect upon the surrounding tissues within the zone of lesion.

Another object of the present invention is to provide favorable conditions to speed up regeneration of bone tissue during consolidation of the bone fragments.

One more object of the present invention is to provide permanent administration of proportioned amounts of medicinal preparations immediately to the zone of regeneration of affected tissues, which results in a substantial saving of medicines used, reduces labour consumption involved in a patient's treatment and cuts down the hospitalization term.

The aforesaid and other objects are accomplished due to the fact that inserts made of a biologically compatible polymer, containing a physiologically active medicine, are made fast in recesses provided in the joining element.

The joining element of the character set forth above is advantageous in that the physiologically active medicine is free to act upon the surrounding tissues immediately either while getting dissolved in the tissue fluid and diffusing through the film of a biologically compatible polymer, or while being set free during the process of biologically destruction of that polymer and acting immediately upon the surrounding tissues. The rate of evolution of the medicinal preparation and the period of its effect in this case depend upon the thickness of the film of a biologically compatible polymer, and may be preset.

Application of the joining elements for fixation of bone tissue, disclosed in the present invention does not involve subsequent administration of physiologically active medicines into the organism either by injection or perorally.

Use of such a joining element enables one to provide high concentrations of physiologically active medicines immediately within the zone of the injured bone tissues and the surrounding soft tissues. This promotes and intensifies the therapeutic effect of the above preparations, reduces the number of postoperative complications and the amount of medicinal preparations consumed, provides for a prolonged action of such preparations and cuts down the term of hospitalization.

According to one of its embodiments the invention provides for application of a rod having longitudinal recesses, with the insert situated on the concave surface of a longitudinal recess.

A hollow rod may also be employed for the purpose, say, one of the Küntscher type. When such is the case the insert of a biologically compatible polymer is made fast in the hollow rod space.

When cover plates are made use of the inserts are secured in dead-end and open-end holes, or in longitudinal slots on the surface adjacent to the bone tissue involved.

4. BRIEF DESCRIPTION OF THE DRAWINGS

In what follows the present invention is exemplified by a description of some specific illustrative embodiments thereof and the accompanying drawings, wherein:

FIG. 1 is a rod having longitudinal recesses, accommodating a biologically compatible polymer, containing a physiologically active medicine;

FIG. 2 is a section taken on the line II—II in FIG. 1;

FIG. 3 is an embodiment of the rod made as a hollow rhomboid cross-section stem (the Küntscher type rod), wherein the biologically compatible polymer, containing a physiologically active medicine is accommodated in the inner channel;

FIG. 4 is a section taken on the line IV—IV in FIG. 3;

FIG. 5 is a joining element shaped as a plate having dead-end and open-end holes, or a slot; and FIG. 6 is a section taken on the line VI—VI in FIG. 5.

5. DESCRIPTION OF THE PREFERRED EMBODIMENTS

Now referring to the appended drawings FIGS. 1 and 2 illustrate a joining element adapted for uniting the fragments of tubular bones and shaped as a rod 1 having a formed outside surface and having stiffening ribs 2 and concave straight segments 3.

An insert 4 made of a biologically compatible copolymer, such as N-vinylpyrrolidone and methylmethacrylate, containing a physiologically active medicinal preparation is made fast by, say, a medicinal adhesive in the hollow space of the rod concave portion. To prolong the effect of the medicinal preparation an additional layer of a biologically compatible copolymer 5 may be applied to the insert. Such rods are applicable for osteosynthesis of tubular bones of any diameter.

The joining element as shown in FIGS. 3 and 4 may be made as a hollow shaped open rod 6 having an interior space 7, e.g., of the Küntscher type. In such a case an insert of a biologically compatible copolymer, containing a physiologically active medicinal preparation is secured in the interior space 7. In cases where use is made of physiologically active substances readily soluble in aqueous media, such as dioxydine, the insert 8 may be covered by a coat 9 of the biologically compatible copolymer in order to retard the rate of liberation of such substances. Such joining elements may be utilized for fixation of fractures of large-diameter tubular bones.

In order to fix transversely fractured bone fragments in the middle third portion of large- and medium-diameter tubular bones (such as the femur, crus, humerus, etc.), use may be made of plates 10 (FIGS. 5 and 6), having a dead-end hole 11 and an open-end hole 13, or a longitudinal slot 16. In such a case inserts 12, 14, and 17 corresponding partly or wholly to the configuration of the holes 11 or 13, or of the slot 16 are made fast in the interior spaces.

To prolong the effect of the physiologically active substance the inserts may likewise be protected with a coat 15 and 18 of a biologically compatible polymer. In this case, like in that of rod-shaped joining elements, the surface of the insert is either arranged below or is made flush with the outside surface of the joining element. This provides for complete intactness of the insert when fixing bone fragments with the joining elements, which is of special importance whenever use is made of rods introduced intramedullary into the tubular bone with the rod diameter exactly corresponding to the diameter of the medullary canal.

Given below are some examples of a practical embodiment of the joining elements for bone tissues with inserts made of biologically compatible polymers, containing physiologically active substances.

EXAMPLE 1

Held to the joining element shaped as a plate having cross-sectional dimensions of 7×30 mm and a length of 120 mm and provided with 30×120 mm holes, by means of a medicinal adhesive, are two cylinders having respective diameters of 2.8 mm and 2 mm and a height of 4 mm, consisting respectively of 0.4 g and 0.24 g copolymer of N-vinylpyrrolidone with methylmethacrylate and containing respectively 0.097 g and 0.067 g dioxydine. After the bone fragments have been fixed a therapeutic level of concentration of the antimicrobial preparation effective within the zone of fracture is kept for 7 to 8 days. The amount of dioxydine consumed when applying a commonly adopted treatment technique (perorally) for the abovesaid period equals 5 to 8 g.

EXAMPLE 2

Three polymer inserts each 0.15 mm thick are formed by the method of casting from a solution in the longitudinal slots of a rod 10 mm in diameter and 400 mm long, having four longitudinal slots with a radius of 3.5 mm and a depth of 1.8 mm, said inserts having a shape following the slot configuration and each containing 0.1 g copolymer of N-vinylpyrrolidone with butylmethacrylate, and 0.04 g quinoxydine, whereupon one of the inserts is coated with a layer of copolymer of N-vinylpyrrolidone with methylmethacrylate 0.08 mm thick. After the rod has been introduced into the fractured bone a prophylactic level of concentration of the medicinal preparation is maintained for 60 to 70 days within the zone of fracture.

EXAMPLE 3

An insert 3 mm thick and 300 mm long is formed from polyglycolic acid by the method of casting from a solution in the slot of the nontruncated sharp edge of a hollow rhomboid cross-section rod having one truncated sharp edge 420 mm and featuring a length of cross-sectional dimensions of 13×13 mm and a wall thickness of 1.4 mm, said polyglycolic acid containing 0.8 g dioxydine, while said insert having a shape following the slot configuration, whereupon a 0.9 mm thick layer of a copolymer of N-vinylpyrrolidone with methylmethacrylate is applied to the insert.

Upon introducing the abovesaid rod into the medullary canal of the fractured bone, a therapeutic level of concentration of the medicinal preparation is maintained for a period of 28 to 39 days within the zone of fracture.

EXAMPLE 4

Four inserts 350 mm long and 0.8 mm thick made of copolymer of acrylamide, ethylacrylate and vinylpyrrolidone, containing 0.8 g potassium orotate, are accommodated in the four respective longitudinal slots 4.0 mm in radius and 2.1 mm provided in a rod 11 mm in diameter and 400 mm long, each of said inserts having a shape following the slot configuration. The entire surface of the insert is coated with a 1.4 mm thick layer of copolymer of N-vinylpyrrolidone with methylmethacrylate. Application of the abovesaid rod cuts down the period of consolidation by 12 to 14 percent, whereas consumption of potassium orotate administered according to the now-adopted technique is within 35 to 40 g.

EXAMPLE 5

Mounted into each of the four longitudinal slots in the rod having a diameter of 8 mm and a length of 350 mm is a 0.6 mm thick insert made of copolymer of N-vinylpyrrolidone with methylmethacrylate, containing 0.25 g orotic acid. Use of such a rod cuts down the period of consolidation of bone fragments by 17 to 20 percent, whereas the consumption of orotic acid when applied to produce a consolidation effect according to the commonly adopted technique, is within 60 to 90 g.

Practical application of the joining elements of the construction alleged in the present invention is capable of: reducing the number of postoperative complications by 20 to 25 percent on the average, and by 40 to 45 percent in case of open fractures; saving medicinal preparations by 45 to 95 percent when rendering medical aid involving administration of physiologically active substances; providing an effective period of medicinal preparations within 02 to 80 days; cutting down hospitalization period by 10 to 40 percent.

What is claimed is:

1. A joining element for fixation of bone tissue comprising: an oblong solid provided with a recess, having an insert made of a biologically compatible polymer containing a physiologically active medicine wherein the outside surface of the insert is coated with a film of a biologically compatible polymer permeable by tissue fluid.

2. A joining element for fixation of bone tissue comprising: an oblong solid provided with a recess having an insert containing a biologically compatible polymer and a physiologically active medicine wherein said insert has an outside surface coated with a film made of a biologically compatible polymer permeable by tissue fluid.

* * * * *